US00PP35975P3

(12) United States Plant Patent
Bouchet

(10) Patent No.: US PP35,975 P3
(45) Date of Patent: Jul. 9, 2024

(54) WHITE PEACH TREE NAMED 'SWEETBINGO'

(50) Latin Name: ***Prunus persica* (L.) Batsch.**
Varietal Denomination: SWEETBINGO

(71) Applicant: AGRO SELECTIONS FRUITS, Elne (FR)

(72) Inventor: Christophe Bouchet, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 18/445,620

(22) Filed: Nov. 28, 2023

(65) Prior Publication Data

US 2024/0180049 P1 May 30, 2024

(30) Foreign Application Priority Data

Nov. 29, 2022 (QZ) ..... PBR 2022/2715

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 5/0868
See application file for complete search history.

*Primary Examiner* — Kent L Bell
(74) *Attorney, Agent, or Firm* — Birch, Stewart, Kolasch & Birch, LLP

(57) ABSTRACT

A new and distinct variety of white peach tree denominated 'SWEETBINGO' which has fruits with high eating quality and very long shelf life without alteration before and after harvesting, with a semi-sweet white flesh at maturity time, having a red pigmentation around the stone cavity, and an attractive skin with a luminous purple red blush on skin surface, on a red background.

7 Drawing Sheets

Botanical classification: *Prunus persica* (L.) Batsch.

Variety denomination: 'SWEETBINGO'.

This application claims priority of Community Plant Variety Right No. 2022/2715 filed on Nov. 29, 2022 which is hereby incorporated by reference in its entirety.

The new variety named 'SWEETBINGO' is also known as 07.05.315.17 PB or ASF2021. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'SWEETBINGO', the provisional reference of this white peach tree variety was 07.05.315.17, corresponding to the tree 315 located in line 05 of the parcel 07 and selected during the year 2017. The letters "PB" are related to the first letters of the type of tree in French (PB for "Pêche Blanche", that means "white peach"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'SWEETBINGO', the clone reference was 'ASF2021'.

BACKGROUND OF THE NEW VARIETY

The present invention relates to a new and distinct variety of white peach tree, *Prunus persica* (L.) Batsch, which has been given the variety denomination 'SWEETBINGO '.

This new tree produces fruits with a long shelf life without alteration both on the tree after growth completion and after harvesting, very good eating quality, semi-clingstone white flesh fruits at maturity, and slightly pinkish under the fruit skin, for fresh market at the end of July or early in August in the Pyrénées-Orientales department, France.

ORIGIN OF THE VARIETY

The 'SWEETBINGO' white peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'SWEETBINGO' variety results from a controlled pollinated cross between the white nectarine named 'NECTARLYS' (not patented) which was used as the seed parent, or female parent, and the yellow peach variety named 'CRISPONDA' (U.S. Plant Pat. No. 28,774) which was used as the pollen parent, or male parent.

The 'SWEETBINGO' variety was obtained by hybridizing and propagated by grafting on a 'INRAR GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree, and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'SWEETBINGO' white peach tree blooms at the beginning of February or mid-February near Elne in the Pyrénées-Orientales department, France. The blooming period is considered early to medium. However, it was observed that its date of blooming seems to be highly dependant on climatic conditions.

The first fruit of 'SWEETBINGO' ripens generally medium in the season, namely during July. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
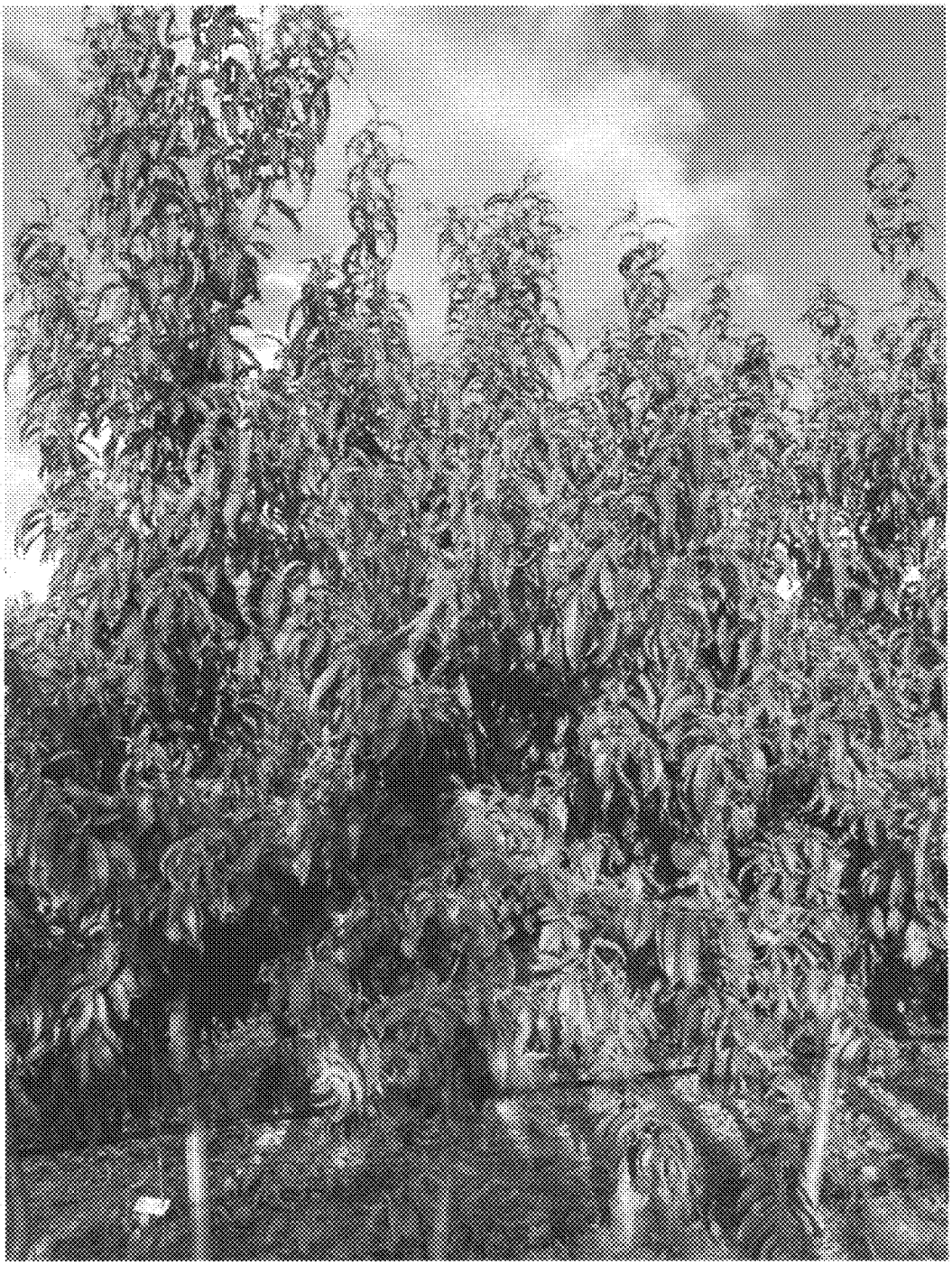
FIG. 1 is a color photograph showing trees of the new variety 'SWEETBINGO' in orchard, bearing fruits.
Figure 2:
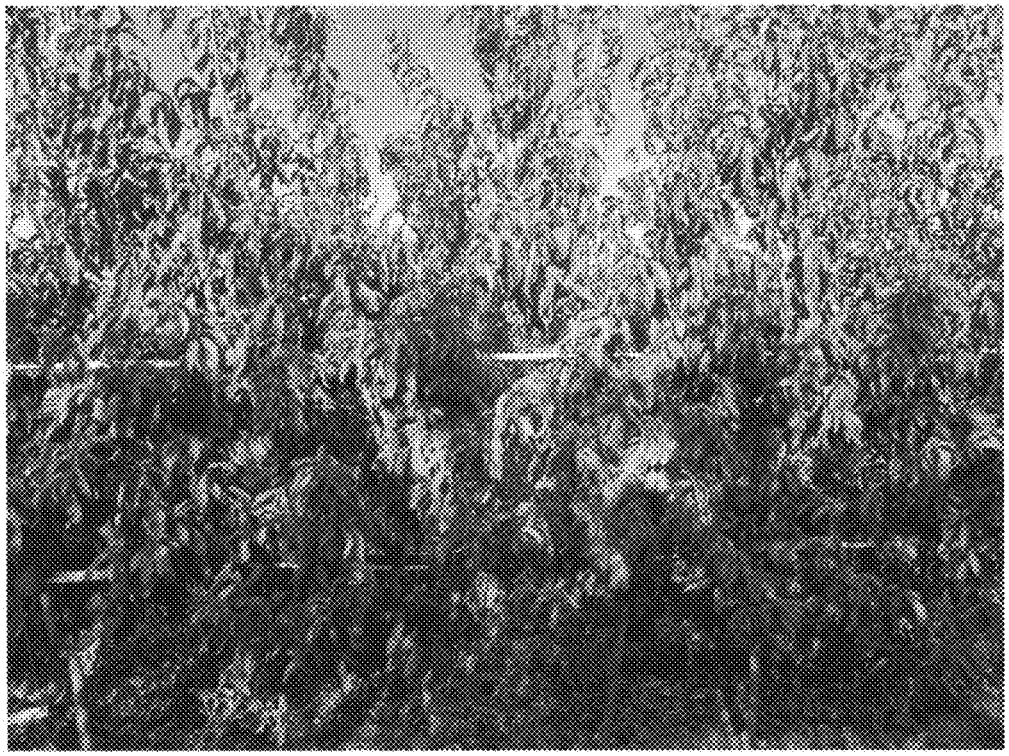
FIG. 2 is a second color photograph showing trees of the new variety 'SWEETBINGO' in orchard, bearing fruits.
Figure 3:
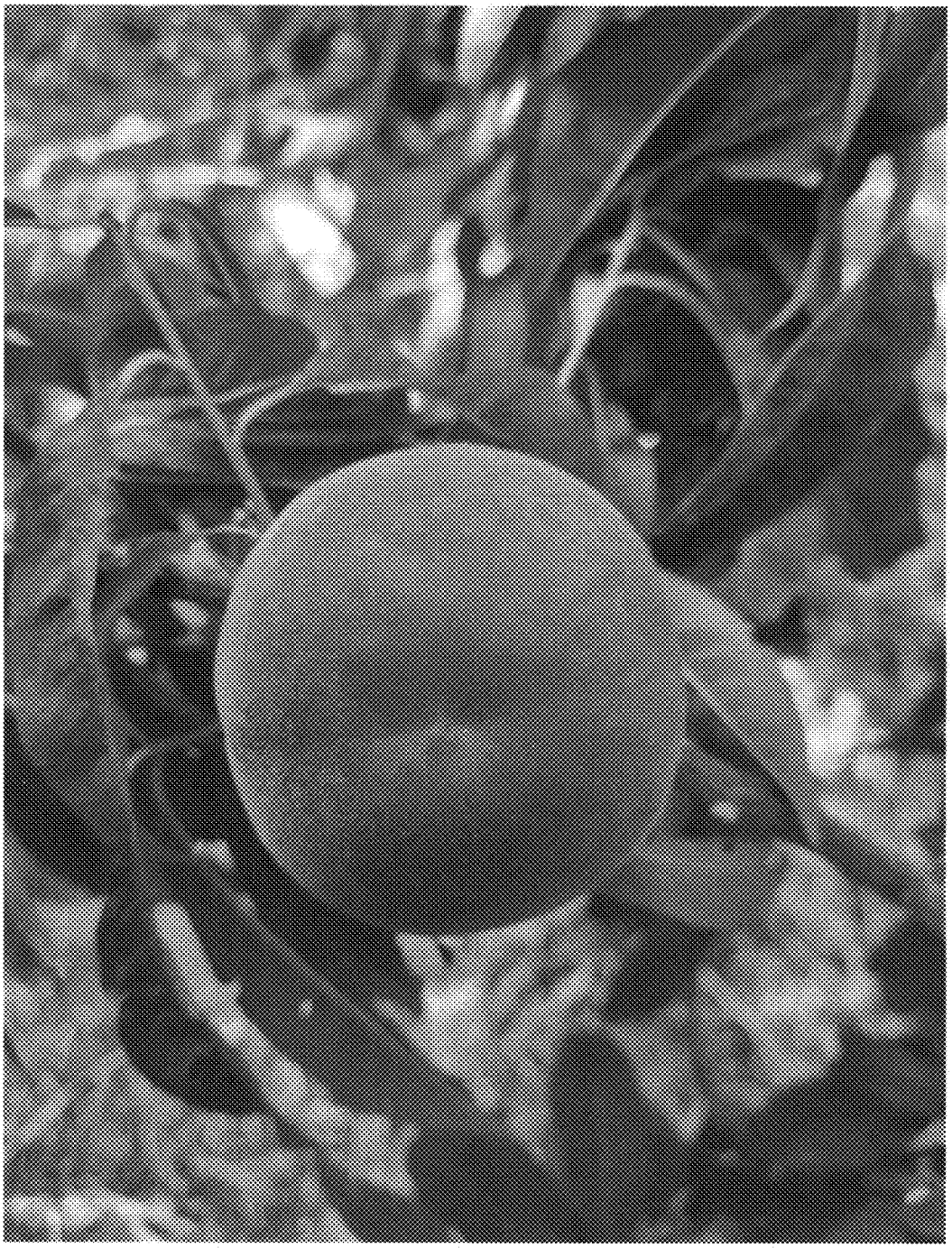
FIG. 3 is also a color photograph showing a close view of a fruit of the new variety in orchard.
Figure 4:
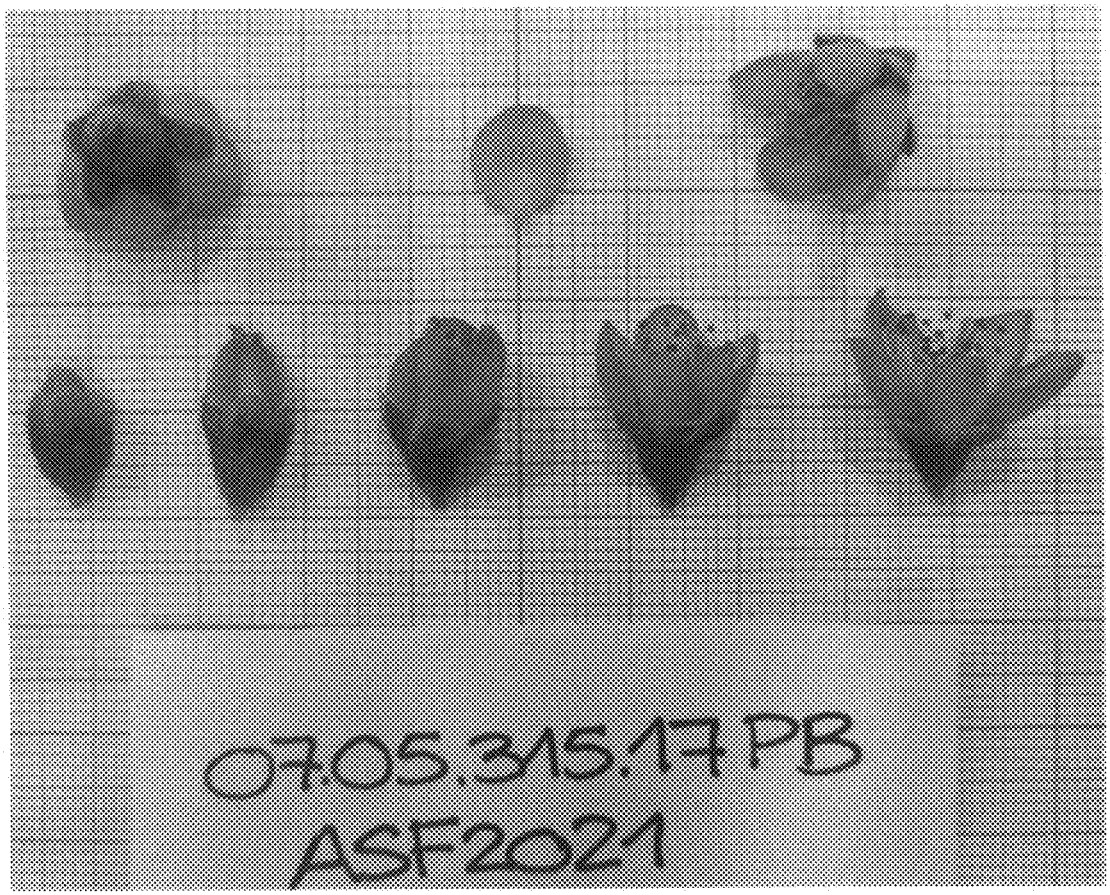
FIG. 4 is a color photograph which depicts the flower buds at different development stages, and the reverse and side views of the flower and the reproductive organs with petals removed, of the new variety 'SWEETBINGO' also named '07.05.315.17 PB' or 'ASF2021' in the figure.
Figure 5:
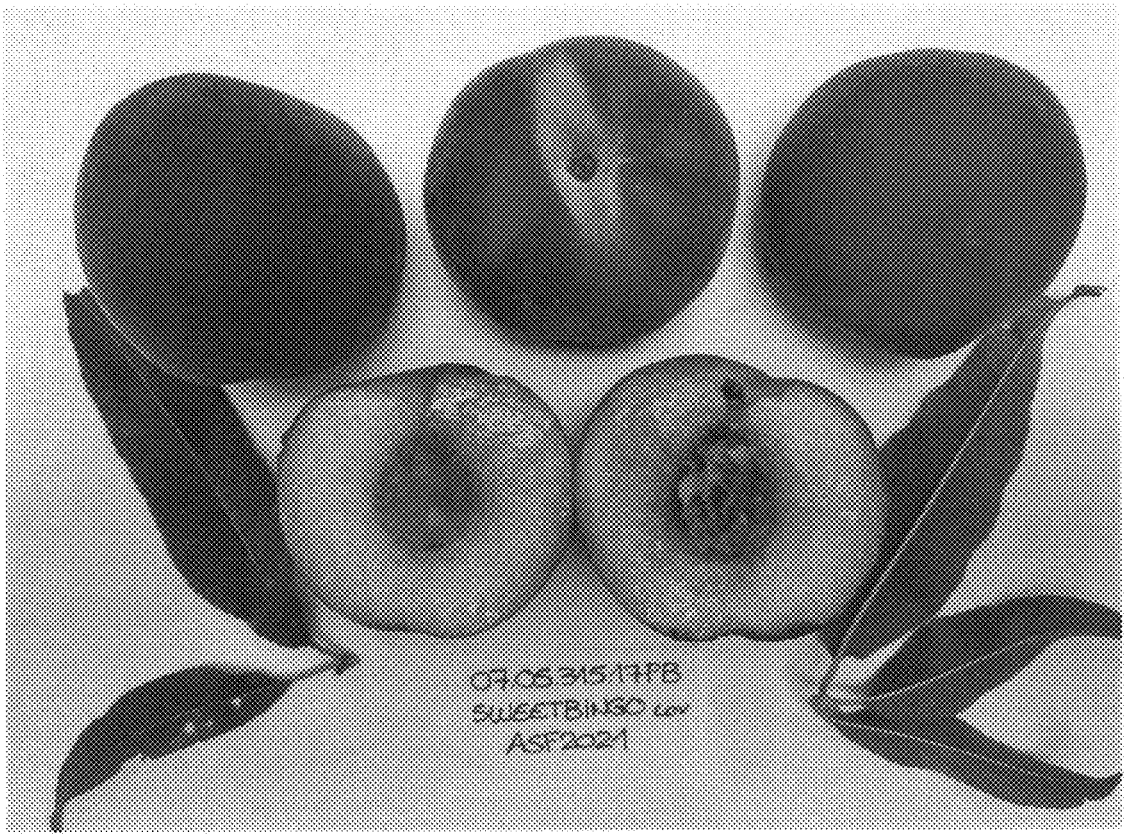
FIG. 5 is a color photograph which shows the upper and lower sides of leaves and different views of four typical specimens of the fruit of the new variety 'SWEETBINGO' also named '07.05.315.17 PB' or 'SWEETBINGO cov' or 'ASF2021', as stated in the figure, at ripening time, one fruit having been cut in half with the pit being left in one of the halves for depicting leaves, fruit flesh, pit and pit cavity of the new variety.
Figure 6:
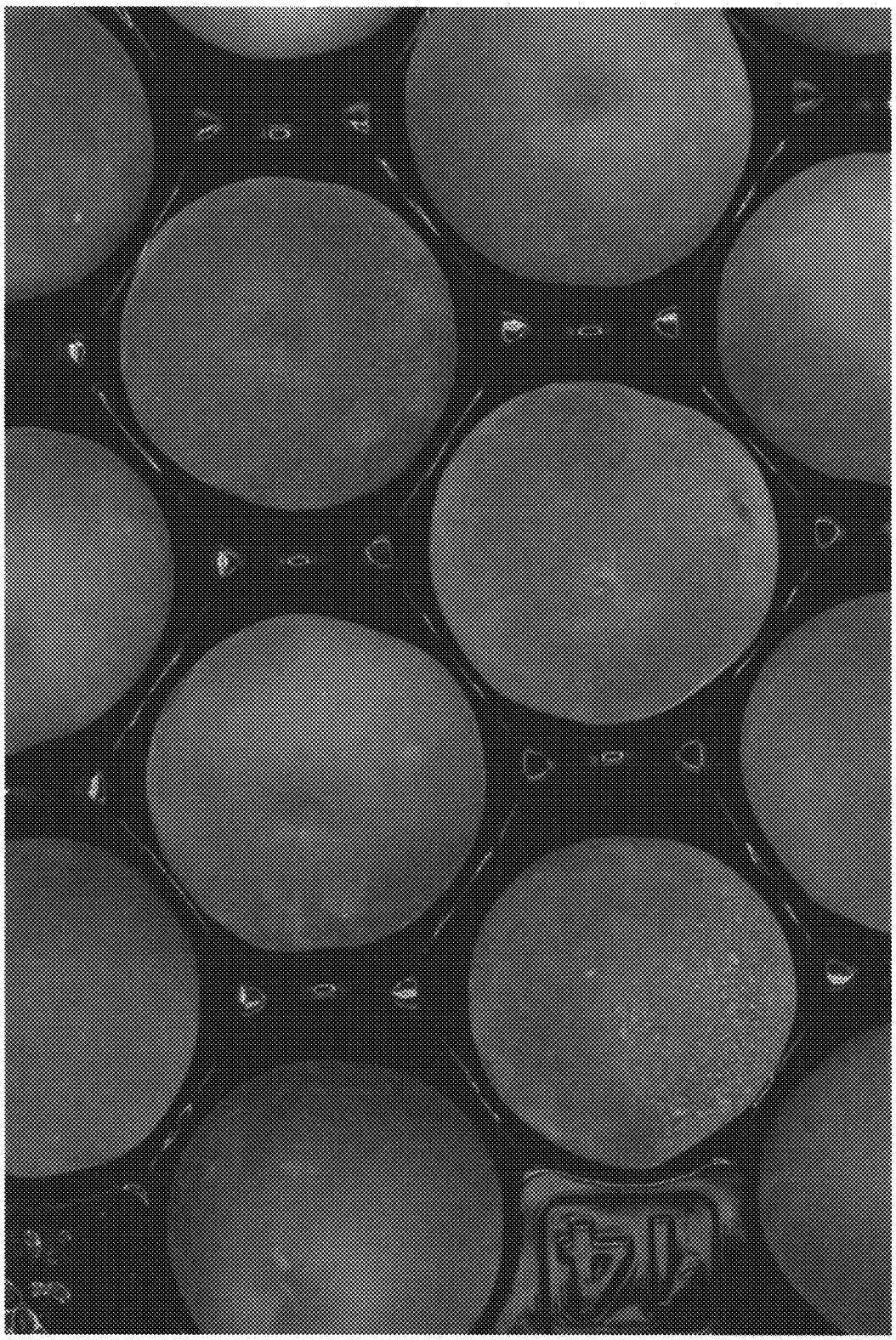
FIG. 6 is a color photograph showing a close view of typical specimens of the fruits of the new variety after harvest.
Figure 7:
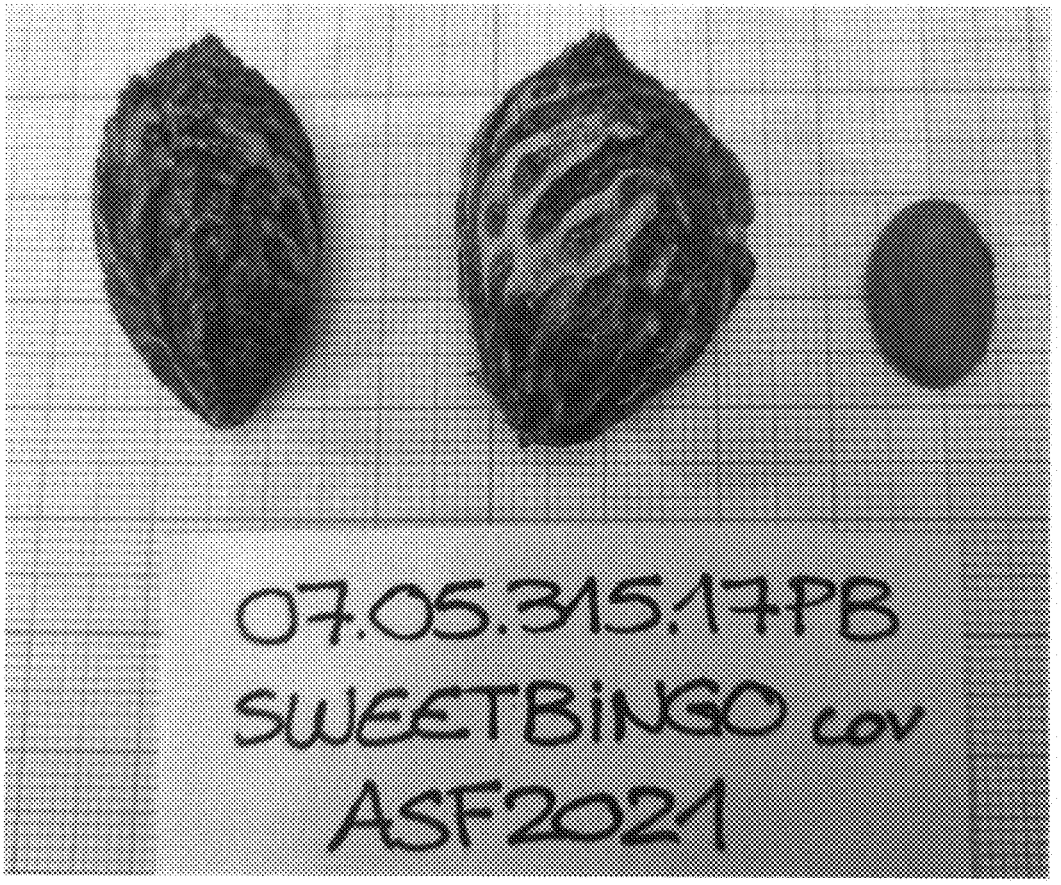
FIG. 7 is a color photograph showing different views of the stone of the new variety 'SWEETBINGO' also named '07.05.315.17 PB' or 'SWEETBINGO cov' or 'ASF2021', as stated in the figure, and the kernel of the stone.

The views of trees, flowers, leaves and fruits have been photographed in their fourth growing season (third year of production).

Due to chemical development, processing and printing, the flowers, stones and fruits depicted in these photographs may or may not be accurate when compared to the actual botanical specimen.

DETAILED BOTANICAL DESCRIPTION

The trees, flowers, and fruits may vary in slight detail due to variations in soil type, cultural practices, and climatic condition. The potential for commercial production of fresh fruits by 'SWEETBINGO' is high, due to fruit very long shelf life without alteration after harvesting.

Trees are medium to strong vigorous and medium to large stature half-standing in a semi-flared out aspect. The anthocyanic coloration of flowering shoot is present excluding brushwood side away from sun. The time of beginning of flowering is considered early to medium; flowering starts during February. The type of flower is campanulate with small petal size. Petals are medium pink. Leaf glands are present and reniform. The fruit flesh is white and may usually show a slightly pinkish pigmentation under the skin, and a red pigmentation radiating around the stone cavity. The fruit skin is thin, with a luminous purple red blush on a purple red background. The new variety 'SWEETBINGO' presents fruits having a good presentation with a nice round shape and a good firmness, with a white flesh having a slightly pinkish pigmentation under the skin and a red pigmentation around the stone cavity, and a good taste for the medium maturity time. The stone is semi-clingstone and its size is medium to large. Fruit taste is semi-sweet, and aromatic.

Compared to 'SWEETCHIEF' white peach variety (not patented), the fruits of 'SWEETBINGO' usually ripen few days later. The fruits of the new variety 'SWEETBINGO' show a rounder shape than the fruits of the 'SWEETCHIEF' variety, as well as a smoother fruit skin. The fruit of the new 'SWEETBINGO' variety, moderately sweet and highly aromatic.

Compared to yellow peach 'CRISPSTAR' variety (not patented), the fruits of the new variety 'SWEETBINGO' usually ripen approximately at the same time. The flowering period of the new variety 'SWEETBINGO' starts approximately one week earlier than the flowering period of 'CRISPSTAR'. The flowers of the new 'SWEETBINGO' variety are campanulate, while the flowers of the similar variety 'CRISPSTAR' are of the rosette type.

It should also be noted that the new 'SWEETBINGO' variety corresponds to a white peach, whereas fruits of the similar variety 'CRISPSTAR' show a yellow flesh. The fruit presentation of the new 'SWEETBINGO' variety is different to that of the similar 'CRISPSTAR' variety, said fruits having a rounder, more homogeneous shape, in comparison with 'CRISPSTAR' fruits which are round and slightly triangular, sometimes mucronate.

Compared to its seed or female parent, i.e., the white nectarine 'NECTARLYS' (not patented) variety, the new variety 'SWEETBINGO' is a white peach. Moreover, the fruits of the new variety 'SWEETBINGO' ripen approximately five to six weeks later than the fruits of 'NECTARLYS'. The flowers of the new variety 'SWEETBINGO' also start to bloom later than the flower of 'NECTARLYS', of about three weeks.

Compared to its pollen parent 'CRISPONDA' (U.S. Plant Pat. No. 28,774) variety, the fruits of the new variety 'SWEETBINGO' ripens approximately five weeks later.

The flowers of the new variety 'SWEETBINGO' also start to bloom a few days later than the flower of 'CRISPONDA'.

DETAILED DESCRIPTION

Referring more specifically to the pomological details of this new and distinct variety of white peach tree, the following was observed on trees in their fourth growing season (third year of production) under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

Tree:

*Size*.—Generally — Considered medium to large. The tree size the first year was approximately 200 to 280 cm in height. The tree was pruned during each following dormant season to a height of approximately 250 cm. Current season shoots growth could reach 80 cm in length. The tree size from the second year (second and next years) reached a final height of 330 cm including current season shoots length. The tree size is consistently reduced to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium to strong.

*Productivity*.—Considered good to very good and regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting fruits, significantly promotes fruit qualities, especially growth, color and firmness. Moreover, contamination risks due to monilia or rot are significantly reduced. 'SWEETBINGO' variety is not much sensitive to cracking of pistil cavity, to cork formation into peduncle cavity or to monilia.

*Bearer*.—Very regular. The fruit distribution is considered homogenous on mixed branches and spurs having more than 1 year. Thinning of 2 fruits out of 3 was necessary for the tree valorisation. Thinning was necessary every year during the years of observation.

*Form*.—The 'SWEETBINGO' variety has naturally a semi-flared shape.

*Density*.—Considered dense.

*Tree branching*.—Medium to strong.

*Hardiness*.—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017,1017 hours in 2017-2018, 844 hours in 2018-2019, 706 hours in 2019-2020, 822 hours in 2020-2021, 700 hours in 2021-2022 and 919 hours in 2022-2023, showed a good behavior of the tree in all cases. No injury with temperatures as low as −12° C. in winter. Good resistance to late frosts.

Trunk:

*Diameter*.—Approximately 44.0 to 50.0 millimeters in diameter when measured at a distance of approximately 20.0 centimeters above the soil level for trees on fourth leaf (or third year of production).

*Bark texture*.—Considered rough, with lenticels.

*Lenticels*.—Lenticels are present. The number of lenticels reaches 1 lenticel per $cm^2$. The lenticels range in size of approximately 4.0 to 5.0 millimeters in width, and about 1.0 to 1.5 millimeters in height.

*Lenticel color*.—The lenticels show a beige color (RHS Greyed Orange 164 A).

*Bark coloration*.—The bark has a brown (RHS Greyed Orange 177 A) to grey color (RHS Grey 201 A) darker than the lenticels color.

Branches:

*Size*.—The branches are pruned to approximately 1.0 meter in length.

*Diameter*.—Average as compared to other peach varieties. The current season shoots have a diameter of approximately 3.0 to 4.0 millimeters, and mature branches (two year's old branches) have a diameter of approximately 7.0 to 9.0 millimeters.

*Surface texture*.—Smooth, despite the presence of small lenticels, for current season shoots and rough, with lenticels, for mature branches, wood which is several years old has furrowed appearance.

*Crotch angles*.—Primary branches are considered variable, but the crotch angles are generally 45 degrees from the horizontal axis for current season shoots and 45° degrees from the horizontal axis for two year's old branches. This particular characteristic is not considered distinctive of the variety, however.

*Current season shoots*.—

*Internode length*.—Generally 17.0 to 20.0 millimeters. Color — The color of new shoot tips is considered green (RHS Yellow Green 145 A) on lower part of new shoot tips, whereas the upper part is darker and colored in purple (RHS Greyed Red 178 A).

*Mature branches*.—

*Internode length*.—Generally between 20.0 and 23.0 millimeters.

*Color of mature branches*.—Brown (RHS Grey Brown N199 C).

*Lenticels*.—Numerous lenticels are present on mature branches. The number of lenticels reaches 2 lenticels per $cm^2$. The size of lenticels is considered small on one year's old shoots and small on two-year-old shoots. The lenticel shape is round with a diameter of approximately 1.0 millimeter on one-year-old shoots. The lenticel shape is stretched round with a diameter of 1.0 to 1.5 millimeters on two-years-old shoots. The lenticels may have a height of approximately 0.5 to 1.0 millimeter and a width of 1.5 to 2.5 millimeters on mature branches.

*Lenticel color*.—The lenticels have a beige color (RHS Greyed Orange 164 A).

Leaves:

*Time of beginning of leaf bud burst*.—Considered medium.

*Size*.—Considered medium for the species. The ratio leaf length/leaf width is 3.621.

*Leaf length*.—The medium length is about 131.25 millimeters with leaf petiole.

*Leaf width*.—The medium width is 36.25 millimeters.

*Leaf form* (*in cross section*).—Concave.

*Leaf form*.—Entire.

*Leaf base shape*.—Acute.

*Leaf tip form*.—Acute.

*Leaf thickness*.—Medium.

*Leaf color*.—Upper leaf surface — Yellow Green (RHS Yellow Green 147 A). Lower surface — A slightly lighter green (RHS Yellow Green 146 A or RHS Yellow Green 146 B) than the upper leaf surface color.

*Leaf texture*.—Smooth and glabrous on both upper and lower surfaces of the leaf.

*Leaf venation*.—Pinnately veined.

*Mid-vein*.—Color — Light green (RHS Yellow Green 144 B to RHS Yellow Green 144 C). Width — Approximately 1.0 millimeter.

*Secondary veins*.—Color — Light green (RHS Yellow Green 145 B or RHS Yellow Green 145 C).

*Leaf margins*.—Slightly undulating.

*Form*.—Considered crenate.

*Uniformity*.—Leaves are isolated or grouped by 2 or 3. In this last case, one leaf of normal size is found with one or two smaller leaves (at least 50% smaller).

*Leaf petioles*.—Size — Considered medium. Length — About 10.0 to about 13.0 millimeters. Diameter — About 1.0 to 1.5 millimeters. Shape — Grooved.

*Petiole color*.—Upper petiole surface — Green (RHS Yellow Green 144 B). Lower surface — A slightly lighter green (RHS Yellow Green 145 A or RHS Yellow Green 145 B) than the upper petiole surface color. Ratio leaf length/petiole length — Approximately 10.

*Leaf glands*.—Size — Considered medium. Their length is about 2.0 millimeters and their width is about 1.0 millimeter. Number — Generally 2 glands per leaf. Type — Reniform. Margins — Smooth and regular. Position — Alternate on the upper part of petiole. Color — On young leaves, leaf glands color is considered a green (RHS Yellow Green 144 C). On older leaves, leaf glands color turns to a brown (RHS Brown 200 B) color.

*Leaf stipules*.—Generally — Leaf stipules have been observed very occasionally. When stipules were observed, they were in pairs, small in size, and with a green color (RHS Yellow Green 144 B or RHS Yellow Green 144 C). But as seen in the characteristic relative to the leaves uniformity, it is possible to find leaves by groups of 2 or 3, with a normal-size leaf and smaller ones.

Flowers

*Flower buds*.—Generally — At pre-floral stage of development, the floral buds are conic in shape. Their form is evolving until blooming, with variable dimensions. Just before blooming, floral buds are approximately 7.0 to 8.0 millimeters wide and approximately 12.0 to 13.0 millimeters long. The floral buds show a homogenous distribution on the trees. Color — This characteristic is dependent upon the proximity to bloom. At pre-floral stage of development, the bottom of the flower's buds, or calyx, or flower receptacle, is of purple color (RHS Greyed Purple 183 A) on its outer face. The inner face of the flower receptacle is greenish yellow (RHS Yellow Green 153 C). The corolla, formed by the petals, is generally of pink color (RHS Red Purple 65 A) on both faces. Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins mid-February. The first bloom was observed on Feb. 7, 2020.

*Blooming time*.—Considered early to medium in relative comparison to other commercial peach cultivars grown in the Pyrénées-Orientales departement, France. The date of full bloom is observed generally at the middle of the blooming period. The date of bloom varies slightly with climatic conditions and cultural practices. Thus, the full bloom was observed in 2020, from February $7^{th}$ until February $17^{th}$, then from February $17^{th}$ to February $25^{th}$ in 2021 and then from February $7^{th}$ to February $13^{th}$, 2022.

*Duration of bloom*.—Medium, approximately between 7 to 11 days. This characteristic varies slightly with the prevailing climatic conditions.

*Flower type*.—The variety is considered to have a campanulate type of flower.

*Flower size*.—Considered small. Flower diameter at full bloom is approximately 20.0 to 21.0 millimeters.

*Bloom quantity*.—Considered high, approximately 40 to 45 flowers per meter, with a high rate of fruit set.

*Flower bud frequency*.—Generally 2 flower buds appear per node, occasionally 1.

*Petal size*.—Generally — Considered small.

*Length*.—Generally between 9.0 and 10.0 millimeters.

*Width*.—Generally between 7.0 and 8.0 millimeters.

*Petal form*.—Elongated.

*Petal count*.—Usually five.

*Petal arrangement*.—Independent.

*Petal texture*.—Smooth on both upper and lower surfaces of the petal.

*Petal color*.—At the stage F of blooming, when the flower is fully opened, both surfaces of the petal are colored with a medium to dark pink (RHS Red Purple 73 B) color when young, becoming slightly darker until the end of blooming.

*Fragrance*.—Light floral fragrance.

*Petal claw*.—Form — The claw is considered to have a narrow form. Length — About 1.0 millimeter. Width — About 1.0 millimeter at the base. Color —

The petal claw usually shows a pink color lighter than the petal color (RHS Red Purple 69 A).

*Petal margins*.—Generally considered smooth.

*Petal apex*.—Generally — The petal apices are generally round shaped.

*Flower pedicel*.—Length — Considered medium and having an average length of approximately 3.0 to 4.0 millimeters. Diameter — Considered average, approximately 1.0 to 2.0 millimeters. Color — Green (RHS Yellow Green 144 B).

*Calyx*.—Internal surface texture — Smooth. Color — At the stage F of blooming, when the flower is opened, the inner surface of the calyx, namely the flower receptacle, is yellow to slightly greenish (RHS Yellow Green 153 C). The outer surface of the calyx is considered of purple color (RHS Greyed Purple 183 A).

*Sepals*.—

*Sepal count*.—Usually 5 sepals. Surface texture — The outer surface has a short, fine pubescent texture. Margins — Smooth Size — Medium. Length — Approximately 5.5 to 6.0 millimeters. Width — Approximately 4.0 to 4.5 millimeters. Form — Conic and round at the top. Color — The upper surface of the sepals shows a purple color (RHS Greyed Purple 183 A) whereas the lower surface of sepals is considered greenish (RHS Yellow Green 144 A).

*Anthers*.—Generally — Small in length, approximately 1 millimeter. Shape — Cordate Color — Depending on the maturity stage, anthers are colored with a red (RHS Red 54 A) to a yellow color (RHS Yellow 9 A).

*Pollen production*.—Pollen is abundant and has a yellow color (RHS Yellow 6 A). The present variety is considered auto-fertile (self-pollinating).

*Pistil*.—Number — Usually 1. Generally — Average in size. Length — Approximately 13.0 to 14.5 millimeters including the ovary. Generally smaller than filaments in length when considered without the ovary. Color — Considered light green (RHS Yellow Green 154 B) at the beginning of blooming period. Position — The pistil is positioned at the same level as the stamens.

*Ovary*.—Height — Approximately 1.5 to 2.0 millimeters. Diameter — Approximately 1.0 to 1.5 millimeters. Color — Light green (RHS Yellow Green 145 A). Pubescence — Absent.

*Stamens*.—Size compared to petals — The size of stamen is higher than the size of petals. Length — Approximately 12.0 to 13.0 millimeters, usually higher than the pistil length (considered without the ovary). Color — White (RHS White 155 A) to pink (RHS Red 56 A) depending on the maturity stage.

*Average number of stamens per flower*.—Approximately 24 to 28 stamens per flower.

*Stigma*.—Diameter — Approximately 1.0 millimeter. Color — Greenish yellow (RHS Yellow Green 154 A or RHS Yellow Green 154 B). Shape — Round. Position of the stigma compared to the anthers — The stigma is at the same level as the anthers.

Fruit:

*Maturity when described*.—Firm to very firm in ripe conditions (shipping ripe).

*Date of first picking*.—Jul. 22, 2019.

*Date of last picking*.—The date of harvest varies slightly with the prevailing climatic conditions. The 'SWEETBINGO' variety has a medium date of picking, and a grouped maturity. The maturity is grouped within 7 to 9 days and the harvest is generally performed in two runs. Picking times carry on from July $22^{nd}$ to Jul. 28, 2019, then from July $5^{th}$ to Jul. 12, 2020, then from July $20^{th}$, to Jul. 28, 2021 and then from July $10^{th}$, to Jul. 18, 2022.

*Size*.—Generally — Homogeneous in size, size 2A. Considered medium.

*Average cheek diameter*.—Approximately 72.0 to 75.0 millimeters.

*Average axial diameter*.—Approximately 67.0 to 73.0 millimeters.

*Width*.—Approximately 77.0 millimeters.

*Typical weight*.—Approximately 165.0 grams. This characteristic is high dependent upon the prevailing cultural practices, and therefore is not particularly distinctive of the variety.

*Fruit form*.—Generally — Round, regular and symmetrical. The fruit is generally uniform in symmetry, viewed from the suture's plane.

*Suture*.—

*Fruit suture*.—The suture is usually not prominent and located from the base to the apex but more pronounced near the base. No apparent callousing or stitching exists along the suture line. Not pointed.

*Ventral surface*.—Form — Smooth.

*Apex*.—slightly depressed. Mucron — Absent. Closing of the pistil cavity — Very good. The pistil cavity is not visible.

*Stem cavity*.—The stem cavity is considered shallow, with a depth of about 12.0 to 15.0 millimeters. Average width is between 10.0 and 11.0 millimeters, and the stem cavity is medium narrow.

*Fruit skin*.—Thickness — Considered thin and strong, and the skin is adherent to flesh. Texture — Almost no pubescence, smooth, very little fluff. Taste — Semi-sweet. Tendency to crack — None observed.

*Color*.—Blush color — This blush color is a uniform luminous purple red (RHS Greyed Purple 187 A). The purple red blush covers approximately 80% of the fruit skin surface on a red background (RHS Greyed Red 179 A) on approximately 20% of the fruit skin surface. The percentage of the blush on the fruit skin surface can vary and is generally dependent upon the prevailing conditions under which the fruit was grown. The pattern of over color of skin is a solid flush. Ground color — The ground color covers approximately 20% of the fruit skin surface, and is considered red (RHS Greyed Red 179 A). Lenticels — No lenticel.

*Fruit stem*.—Short in length, thick and strong. Approximately 6.0 to 8.0 millimeters in length. No tearing or detachment.

*Diameter*.—Approximately 5.0 millimeters.

*Color*.—Pale green (RHS Yellow Green 145 A).

*Flesh*.—Ripens — Very homogenously, slowly, with a grouped maturity. The flesh has a long shelf life. Texture — Firm to very firm, crunchy, melting, at harvest maturity stage. Fibers — Not fibrous. Aroma — Considered present, with no further characterization. Eating quality — Considered very good, semi-sweet and aromatic. Flavor — Considered semi-sweet. The Brix is generally superior to 13, with values between 13.1 and 14.2, and an average value at 13.7, and acidity is low. Juice — Juicy at complete maturity. The juice is usually colourless or slightly cream color (RHS NN155 D). Brix — The medium Brix is 13.7 degrees. This characteristic varies slightly between 13.1 and 14.2 with the number of fruits per tree, prevailing cultural practices and the surrounding climatic conditions. Flesh color — The flesh is considered white (RHS White 155 A), with a red pigmentation (RHS Red 47 A) radiating around the stone cavity. Red coloration of flesh next to skin — Slightly pinkish (RHS Red 37 B).

Stone:

*Type*.—Semi-Clingstone, more or less semi-adherent depending on the fruit maturity.

*Size*.—Considered medium to large for the variety. The stone size varies significantly depending upon the tree vigor, crop load and prevailing growing conditions.

*Length*.—Approximately 33.0 to 35.0 millimeters.

*Width*.—Approximately 24.0 to 25.0 millimeters.

*Diameter*.—Approximately 18.0 to 20.0 millimeters.

*Form*.—Obovate.

*Base*.—Oblique.

*Apex*.—Shape — The stone apex is pointed. Shape of stem tip — Ovate.

*Stone cavity*.—Considered medium in size, with obovate form similar to the stone's shape, and dimensions corresponding to the stone dimensions (approximately 33.0 to 35.0 millimeters in length, 24.0 to 25.0 millimeters in width and 18.0 to 20.0 millimeters in diameter).

*Stone surface*.—Surface texture — The pit is transversely furrowed on its entire surface. Furrows are deeper and more oblate on lateral sides. Ridges — The surface texture is generally characterized by more prominent ridges along the ventral edges and at the apical tip.

*Ventral edge*.—Width — Narrow. Approximately 1.0 millimeter at mid-suture.

*Dorsal edge*.—Shape — Grooved.

*Stone color*.—The color of the dry stone is generally considered light brown to beige (RHS Greyed Orange 164 B or RHS Greyed Orange 164 C).

*Tendency to split*.—Splitting is absent.

*Kernel*.—Size — The kernel is considered large. Length — Approximately 17.0 millimeters. Width — Approximately 11.0 millimeters. Thickness — Approximately 6.0 millimeters. Form — Considered obovate. Pellicle — The pellicle of the kernel has a short pubescence. Color — The kernel skin is light brown colored (RHS Greyed Orange N167 A). The almond, which is the seed of the kernel, is white (RHS White NN 155 A) and has a sweet taste. The kernel and its embryo are mature at the time of fruit maturity.

*Use*.—The subject variety 'SWEETBINGO' is considered to be a white peach tree having a medium season of maturity, and which produces fruits that are considered firm, attractively colored with a luminous purple red. Fruits have semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

*Keeping quality*.—Remarkable. Fruits have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality*.—Considered very good. The fruit of the new white peach variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease*.—No particular susceptibilities were noted. The present variety is not very sensitive to Monilia or rot. The pistil cavity is completely closed, generally without any cork formation.

Although the new variety of white peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white peach tree named SWEETBINGO as illustrated and described, characterized by fruits with high eating quality and very long shelf life without alteration before and after harvesting, with a semi-sweet white flesh at maturity time having a red pigmentation around the stone cavity, and an attractive skin with a luminous purple red blush on skin surface, on a red background.

* * * * *